United States Patent [19]
Temin et al.

[11] 3,991,008
[45] Nov. 9, 1976

[54] DENTAL COMPOSITIONS HAVING IMPROVED COLOR STABILITY

[75] Inventors: Samuel C. Temin, Needham; Mildred C. Richards, Wakefield, both of Mass.

[73] Assignee: The Kendall Company, Boston, Mass.

[22] Filed: Aug. 12, 1974

[21] Appl. No.: 496,769

[52] U.S. Cl.............................. 260/42.15; 260/42.29; 260/42.52; 260/998.11
[51] Int. Cl.²...................... C08K 5/54; C08K 5/36
[58] Field of Search.......... 260/998.11, 42.52, 42.29, 260/86.5 A, 89.5 S, 42.15

[56] References Cited
UNITED STATES PATENTS

| | | | |
|---|---|---|---|
| 2,558,139 | 6/1951 | Knock et al. | 260/998.11 |
| 3,539,533 | 10/1970 | Lee et al. | 260/42.52 |
| 3,625,916 | 12/1971 | Newman | 260/42.29 |
| 3,709,866 | 1/1973 | Waller | 260/42.52 |
| 3,832,326 | 8/1974 | North et al. | 260/42.29 |
| 3,845,009 | 10/1974 | Gander | 260/42.52 |

*Primary Examiner*—V.P. Hoke
*Attorney, Agent, or Firm*—Ellen P. Trevors

[57] ABSTRACT

Dental compositions having improved color stability are prepared by employing a redox catalyst system consisting of a hydroperoxide oxidizing agent and a substituted thiourea reducing agent. The composition also comprises a methacrylate monomer, and optionally, a filler and a coupling agent.

16 Claims, No Drawings

DENTAL COMPOSITIONS HAVING IMPROVED COLOR STABILITY

This invention relates to dental compositions having improved color stability. More particularly, this invention relates to polymerizable dental compositions containing a redox catalyst system consisting of a hydroperoxide oxidizing agent and a substituted thiourea reducing agent and to the cured compositions made therefrom.

Polymerizable dental compositions based on methacrylate monomers are used as fillings, pit and fissure sealants, etc. One of the problems encountered with such compositions is a lack of color stability, that is, stability to ultraviolet light. The curing systems conventionally used for restorative composites utilize, as the reductant portion of the redox initiator, various aromatic amines. These aromatic amines lead to color formation particularly under the influence of sunlight and other sources of ultraviolet radiation. A serious aesthetics problem arises as the restoration gradually changes from the tooth matching shade or color; a distinct and unattractive differentiation between the tooth and the restoration may become obvious in a matter of months. Efforts to minimize the deleterious color changes brought about by the amines have been sought by chemically modifying the amines as described by R.L. Bowen and H. Argentar in J. Am. Den. Assoc., Vol. 75, No. 4, p. 918–923 (Oct. 1967). Nevertheless, total color stability cannot be achieved with any of the aromatic amine systems, and it is necessary in conventional composites to incorporate ultraviolet stabilizers to minimize color formations. However, the addition of such non-polymerizable, low molecular weight ingredients which are potentially capable of leaching, and hence, of pulpal irritation, is undesirable.

Conventional restorative composites also use peroxides, most commonly benzoyl peroxide, as the oxidant part of the redox initiator system. Benzoyl peroxide has a low half-life, resulting in poor shelf-life stability. Thus, if one per cent of benzoyl peroxide is dissolved in methyl methacrylate or triethylene glycol dimethacrylate or the like, and the solution allowed to stand at room temperature, polymer is formed within a week. To retard premature polymerization, such composites are generally stored by the dentist in a refrigerator.

Redox systems employing certain hydroperoxides and thioureas have previously been described in the literature. Thus, U.S. Pat. No. 3,591,438 discloses bonding accelerators comprising an aldehyde-amine condensation product and a reducing activator such as 1-allyl-2-thiourea to accelerate the cure of a peroxy (including hydroperoxy) initiated acrylate-based adhesive or sealant composition. While functional for the intended purpose, the aforementioned three-component accelerator produces colored compositions.

T. Sugimura et.al., in J. Poly. Sci., Vol. 3, p. 2935–2945 (1965) report the polymerization of acrylonitrile with t-butyl hydroperoxide and thiourea and such substituted thioureas as diphenyl-, ethylene-, diacetyl-, monoacetyl- and diethyl thiourea.

Now it has been found in accordance with this invention that dental compositions based on polymerizable methacrylate monomers can be polymerized employing a hydroperoxide oxidizing agent and a substituted thiourea reducing agent to provide a cured composition of enhanced color stability. This redox system also affords an eminently acceptable rate of cure for the monomer, a major consideration in this application. Furthermore, the composition of the present invention has enhanced shelf-life stability due to the hydroperoxide component and does not require storage in a refrigerator.

More in detail, the polymerizable dental composition of this invention comprises 20–100 parts by weight of at least one methacrylate monomer having 2 to 4 polymerizable double bonds, 0–80 parts by weight of an inorganic particulate filler, 0–5.0% by weight based on said methacrylate monomer of a silane coupling agent, 0.5–5.0% by weight based on said methacrylate monomer of a hydroperoxide oxidizing agent and 0.3–2.0% by weight based on said methacrylate monomer of a substituted thiourea reducing agent. For application as a dental composite, the composition of this invention preferably comprises 20–25 parts by weight of the methacrylate monomer or monomers, 75–80 parts by weight of the filler, 3.0–5.0% by weight based on said methacrylate monomer of silane coupling agent, 2.0–3.0% by weight based on said methacrylate monomer of a hydroperoxide oxidizing agent and 0.5–1.0% by weight based on said methacrylate monomer of a substituted thiourea reducing agent.

The hydroperoxide oxidizing agent is characterized by having the peroxy group attached to a tertiary carbon atom. Exemplary hydroperoxides are those having the formula

wherein R is t-butyl, cumyl, p-methane or p-isopropyl cumyl. Preferably the composition contains 1.0 to 2.0% by weight of oxidizing agent.

The reducing agent employed in this invention is a substituted thiourea having the formula

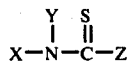

wherein X is H or Y and Y is alkyl having 1 to 8 carbon atoms, such as methyl, butyl, octyl; cycloalkyl having 5 or 6 carbon atoms such as cyclopentyl, cyclohexyl; chloro, hydroxy or mercapto substituted alkyl having 1 to 8 carbon atoms such as chloroethyl, mercapto-ethyl, hydroxymethyl and chlorooctyl; alkenyl having 3 to 4 carbon atoms, such as allyl or methallyl; aryl having 6 to 8 carbons, such as phenyl or xylyl, and chloro-, hydroxy-, methoxy-, or sulfonyl substituted phenyl such as chlorophenyl, phenylsulfonyl, hydroxyphenyl and methoxyphenyl; acyl having 2 to 8 carbon atoms such as acetyl, butyryl, octanoyl; chloro or methoxy substituted acyl, such as chloroacetyl, chlorobenzoyl, chlorotoluoyl and methoxybenzoyl; aralkyl having 7 to 8 carbon atoms, such as benzyl, or chloro or methoxy substituted aralkyl such as methoxybenzyl; and Z is $NH_2$, NHX or $NX_2$. Examples of illustrative compounds suitable for use in the practice of this invention are methyl thiourea, isopropyl thiourea, butyl thiourea, octyl thiourea, benzyl thiourea, acetyl thiourea, benzoyl thiourea, octanoyl thiourea, cyclohexyl thiourea, allyl thiourea, 1,1,3-triphenyl thiourea, 1,1,3-trimethyl thiourea, 2,4-xylyl thiourea, p-tolylsulfonyl thiourea, 1-octyl-3-phenyl thiourea, o-methoxyphenyl thiourea, m-hydroxyphenyl thiourea, 1,1-diallyl thiourea, 1,3-diallyl thiourea, 2-methallyl thiourea, o-methoxybenzyl thiourea, 1-(hydroxymethyl)-3-methyl thiourea, 1,1- dibutyl thiourea, 1,3-dibutyl thiourea, 1-(p-chlorophenyl)-3-methyl thiourea, 1-butyl-3-butyryl thiourea, 1-acetyl-3-phenyl thiourea, 1-methyl-3-(p-vinylphenyl) thiourea, 1-methyl-3-o-tolyl thiourea, 1-methyl-3-pentyl thiourea, 3-methyl-1,1-diphenyl thiourea and 1-acetyl-3-(2-mercaptoethyl) thiourea. While any of the aforementioned thioureas can be employed in the practice of this invention, preferred are the monosubstituted thioureas, that is, those having the aforementioned formula wherein X is H and Z is $NH_2$. Particularly preferred are phenyl thiourea, acetyl thiourea and allyl thiourea. Preferably, the composition contains about 0.5 to about 1% by weight of reducing agent.

The methacrylate monomer is selected from materials having at least two, and preferably two to four polymerizable double bonds per molecule in order that the cured composite be crosslinked and thus better suited for use in the oral cavity. The most preferred monomers are those having two polymerizable double bonds per molecule. Desirable characteristics for such monomers include low polymerization shrinkage, low exotherm during polymerization, low water sorption and the ability to cure rapidly and completely in the mouth. It is also desirable that the monomers be low in volatility and non-irritating to the pulp.

Methacrylate monomers particularly useful in this invention are those represented by the following general formulae:

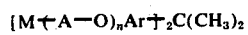      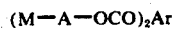

I            II

        

III      IV      V

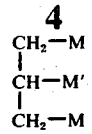

VI wherein M is methacryloyloxy, i.e., $CH_2=C(CH_3)COO-$; M' is methacryloyloxy or hydroxyl; A is alkylene having 1–3 carbon atoms, such as methylene, propylene, isopropylene, hydroxyalkylene having 1–3 carbon atoms, such as hydroxymethylene, 2-hydroxypropylene or acetoxyalkylene having 3 to 5 carbon atoms in the alkylene group such as 2-acetoxypropylene, 3-acetoxyamylene etc.; $n$ is zero or 1; $m$ is 2 or 3 and $o$ is 1 or 2 with the proviso that the sum of $m$ and $o$ is 4; R is hydrogen, methyl, ethyl or —A—M wherein A and M are previously described; Ar is phenylene, e.g., o-phenylene, m-phenylene or p-phenylene, alkyl substituted phenylene, e.g., tolylene or 5-t-butyl-m-phenyolene or cycloalkylene having 6 to 10 carbon atoms such as 1,3-cyclohexylene; and $R^1$ is alkylene having 2 to 12 carbon atoms such as ethylene, dodecylene etc. or $-R^2(O-R^2)_xOR^2-$ wherein $R^2$ is alkylene having 2 or 3 carbon atoms such as ethylene, propylene or isopropylene and $x$ is zero to 5; and $R^3$ is phenylene, tolylene, methylene-bis-phenylene or alkylene having 2 to 12 carbon atoms.

Monomers having the above formulae are well known and generally commercially available materials. Alternately, they are readily provided by conventional synthetic routes, for example, by reacting a phenolic compound such as diphenolic acid, phloroglucinol or bisphenol A with glycidyl methacrylate in the presence of various tertiary amines or by reacting methacrylic acid with an epoxide containing compound such as the diglycidyl ether of a bisphenol. Some of these monomers also are made by reacting appropriate alcohols with methacrylic acid, methacrylyl chloride or methacrylic anhydride.

Illustrative monomers having these formulae include:

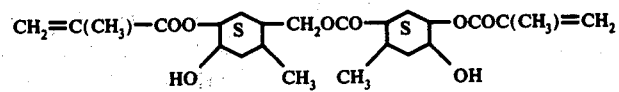

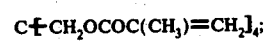

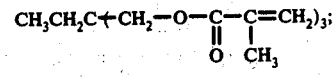

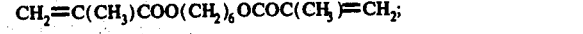

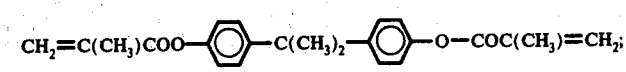

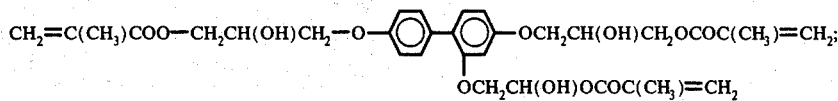

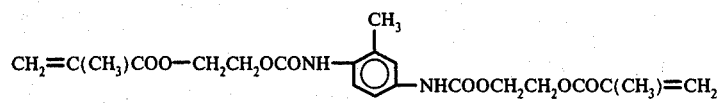

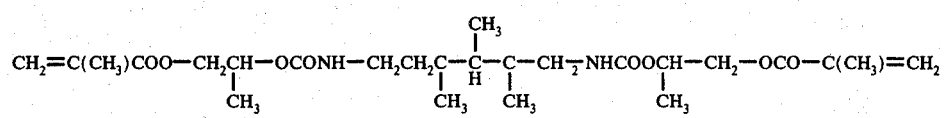

Monomers having the formulae I, II, III and IV are preferred in the practice of this invention. Of these monomers, I, II and III are particularly preferred, monomers IV being employed more often in admixture with one or more of monomers, I, II and III.

Other useful methacrylate monomers suitable for use in the practice of this invention include those having the following formulae wherein M and Ar are as previously described;

$(MR^4OAr)_2C(CH_3)_2$ wherein $R^4$ is isopropylene; $(MR^5OAr)_2$ and $(MR^5O)_2Ar$ wherein $R^5$ is 2-hydroxypropylene; $MAOR^6M$ wherein $R^6$ is hydroxycyclopentyl; $M-A'-R^7M$ wherein $A'$ is hydroxycyclohexyl and $R^7$ is 2-hydroxyethylene; and $M_2R^8$ wherein $R^8$ is

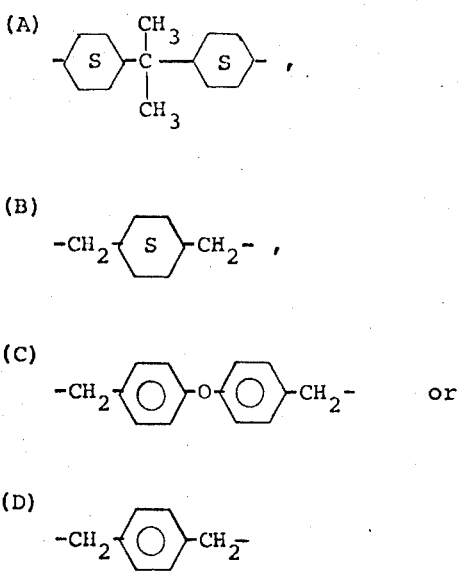

Generally these monomers are commercially available. Preparative details for many of these monomers are given in U.S. Pat. Nos. 3,066,112; 3,721,644; 3,730,947; 3,770,811 and 3,774,305. A tertiary eutectic monomer mixture also suitable for use in this invention is described in U.S. Pat. No. 3,539,526. All of the aforementioned patents are herewith incorporated by reference in their entirety.

It is to be understood that mixtures of two or more appropriate methacrylate monomers are within the scope of this invention. In fact, depending on the choice of monomers, mixture are often highly desirable to optimize the characteristics of the resulting dental composition. Thus, it is preferred that the monomer or monomer blend have a viscosity of from about 100 to about 20,000 centipoises as determined using a Brookfield viscometer at 20 rpm at room temperature. More viscous masses are conveniently handled at higher temperatures.

The inorganic particulate filler employed in the compositions of this invention include fused silica, quartz, crystalline silica, soda glass beads, glass rods, ceramic oxides, particulate silicate glass and synthetic minerals such as beta-eucryptite ($LiALSiO_4$), the latter having negative thermal expansions. It is also feasible to employ finely divided materials and powdered hydroxylapatite, although materials that react with silane coupling agents are preferred. Small amounts of pigments to allow matching of the composition to various shades of teeth can be included. Suitble pigments include iron oxide black, cadmium yellows and oranges, fluorescent zinc oxides, titanium dioxide, etc. The filler particles would be generally smaller than about 50 microns in diameter and preferably smaller than 30 microns. It will be noted that the filler is an optional ingredient, unfilled formulations being employed where the dental composition is intended for use as a coating, margin sealant for amalgam restorations or adhesive.

The silane coupling agents or keying agents are materials that contain at least one polymerizable double bond to react with the methacrylate monomers. Examples of suitable coupling agents are vinyl trichlorosilane, tris(2-methoxyethoxy) silane, tris(acetoxy) vinyl silane, 1- N-(vinylbenxylaminoethyl)aminopropyl trimethoxysilane-3 or 3-methacryloxypropyl trimethoxy silane. The last named material is preferred for use with methacrylate monomers because of the similarity in reactivity of the double bonds.

The compositions of this invention are readily prepared by conventional mixing techniques. Generally the methacrylate monomer or monomers is mixed with the silane coupling agent and the reducing agent. Then the inorganic particulate filler is added and mixed to a paste. This paste is supplied to the dentist together with oxidizing agent packaged separately. Accompanying instructions advise the dentist to mix an appropriate amount of oxidizing agent with the paste and then use the composition for the intended application, allowing the cure to take place in the oral cavity.

In another technique, the silane coupling agents can be bonded or applied to the inorganic particulate filler before the latter is blended with the monomer. This can be accomplished by acid hydrolysis or alkaline hydrolysis, for example, by following the procedure described in U.S. Pat. No. 3,066,112.

The following examples will serve to illustrate the practice of this invention.

EXAMPLE 1

A. Preparation of Composition

A homogeneous solution having the following composition was prepared by mixing the ingredients at room tempeature:

71 parts BIS-GMA (the reaction product of bisphenol A and glycidyl methacrylate, otherwise identified as bis[4-(2-hydroxy-3-methacryloxypropyl)-phenyl] propane-2);

29 parts polyethylene glycol dimethacrylate having an average molecular weight of polyethylene glycol of 200;

5 parts γ-methacryloxypropyl trimethoxysilane; and 1.05 parts allyl thiourea.

To the amount of 2.0 g. of this homogeneous solution was added 5.5 g. of noncrystalline colorless fused silica which had been previously washed with 20% hydrochloric acid solution to remove metallic impurities and which passes a number 325 U.S. Standard sieve. Upon mixing, a homogeneous paste was obtained. Then 0.004 g. of cumene hydroperoxide (in a small amount of 1,6-hexanediol dimethacrylate) was added with spatulation to a 0.8 gm. portion of the homogeneous paste and the sample placed in a polytetrafluoroethylene mold and allowed to cure for approximately 3 minutes. The resulting circular sample had a diameter of ⅝ inch and a thickness of 1/16 inch.

B. Color Stability Testing

Testing for color stability was carried out using the ultraviolet source described in American Dental Association Specification No. 12 for Denture Base Polymer with the following modifications. A round quartz window cooled by a water layer 1 cm. in depth was placed under the light source in order to eliminate infrared light. A General Electric RS sunlamp which had been in use for 100 hours prior to this testing was employed as the lamp. The distance from bulb to turntable was 250–300 mm. To commence the test, half of the button was shielded from the light by covering it with aluminum foil, the covered portion served as the control. The button was exposed to ultraviolet light for 55 hours but no change in color was observed upon comparing the covered part of the sample with the uncovered part. The test was terminated at this point. (This test specifies that the uncovered sample shall not show more than a slight change in color after exposure for 24 hours.)

EXAMPLES 2–12

The general procedure of Example 1 was followed in preparing the compositions of Examples 2–12; the ingredients and proportions employed in these compositions are listed in Table I. The amount of homogeneous solution taken to prepare the paste varied slightly in the examples, but the amount of paste placed in the mold remained constant in accordance with Example 1. Thus, the oxidant and reductant are given in the table as per cent by weight of the amount of total monomer (major monomer and diluent monomer) employed in the composition. Filler is listed as per cent by weight of total composition. The hydroperoxide was always added as a solution in 1,6-hexanediol dimethacrylate to facilitate the addition of small amounts. The fused silica and BIS-GMA used in these examples are as defined in Example 1. A selection of these compositions were tested for color stability employing the equipment and method described in Example 1; these results are set forth in Table II.

TABLE I

| | Homogeneous Solution Ingredients | | | | | |
|---|---|---|---|---|---|---|
| Example | Major Monomer (parts by Weight) | Diluent Monomer (parts by weight) | Coupling Agent (parts by weight) | Reductant % by Weight of Total Monomer | Oxidant % by Weight of Total Monomer | Filler % by Weight of Total Composition |
| 2 | BIS-GMA (71) | HMDMA[1] (29) | MPTS[2] (5) | acetyl thiourea (1.0) | cumene hydroperoxide (2.0) | fused silica (73) |
| 3 | BIS-GMA (71) | PEGDMA[3] (29) | MPTS[2] (5) | acetyl thiourea (1.0) | p-methane hydroperoxide[4] (4.5) | fused silica (78) |
| 4 | HBPDMA[5] (50) | BGDMA[6] (50) | MPTS[2] (5) | acetyl thiourea (0.9) | cumene hydroperoxide (2.0) | fused silica (73) |
| 5 | TMETMA[7] (50) | BGDMA[6] (50) | MPTS[2] (5) | allyl thiourea (0.9) | cumene hydroperoxide (3.0) | fused silica (73) |
| 6 | BIS-GMA (50) | TEGDMA[8] (50) | MPTS[2] (5) | acetyl thiourea (1.0) | cumene hydroperoxide (2.0) | pigmented amorphous silica (75) |
| 7 | BMIP[9] (50) | HMDMA[1] (50) | MPTS[2] (5) | acetyl thiourea (1.0) | cumene hydroperoxide (2.0) | amorphous silica (75) |
| 8 | BIS-GMA (71) | HMDMA[1] (29) | MPTS[2] (5) | phenyl thiourea (1.0) | cumene hydroperoxide (2.0) | amorphous silica (73) |
| 9 | BIS-GMA (71) | TEGDMA[8] (29) | MPTS[2] (5) | 3-allyl-1, 1-diethyl-thiourea (1.0) | cumene hydroperoxide (2.0) | amorphous silica (73) |
| 10 | BIS-GMA (71) | TEGDMA[8] (29) | MPTS[2] (5) | acetyl thiourea (1.0) | diisopropyl-benzene hydroperoxide[4] (2.0) | fused silica (78) |
| 11 | BIS-GMA (71) | TEGDMA[8] (29) | MPTS[2] (5) | acetyl thiourea | p-menthane | fused silica |

TABLE I-continued

Homogeneous Solution Ingredients

| Example | Major Monomer (parts by Weight) | Diluent Monomer (parts by weight) | Coupling Agent (parts by weight) | Reductant % by Weight of Total Monomer | Oxidant % by Weight of Total Monomer | Filler % by Weight of Total Composition |
|---|---|---|---|---|---|---|
| 12 | BIS-GMA (71) | TEGDMA[8] (29) | MPTS[2] (5) | acetyl thiourea (1.0) | hydroperoxide[4] (1.0) (4.0) t-butyl hydroperoxide (4.0) | fused silica (78) (78) |

[1] HMDMA = 1,6-Hexanediol Dimethacrylate
[2] Coupling agent —δ-Methacryloxypropyl Trimethoxysilane
[3] PEGDMA = Polyethylene Glycol Dimethacrylate
[4] A product of Hercules, Inc., Wilmington, Delaware
[5] HBPDMA = Hydrogenated Bisphenol A Dimethacrylate
[6] BGDMA = 1,3-Butylene Glycol Dimethacrylate
[7] TMETMA = 1,1,1-Trimethylolethane Trimethacrylate
[8] TEGDMA = Triethyleneglycol Dimethacrylate
[9] BMIP = Bis(2-methacryloxyethyl)isophthalate

TABLE II

| Example | Exposure (hours) to Perceive Color Change |
|---|---|
| 2 | >55 |
| 3 | >24 |
| 4 | >24 |
| 5 | slight after 28 |
| 6 | >32 |
| 7 | >28 |
| 8 | not tested |
| 9 | not tested |
| 10 | barely perceptible after 31 |
| 11 | noticeable after 31 |
| 12 | >31 |

EXAMPLE 13

Seventy-one parts of BIS-GMA (identified in Example 1), 29 parts of triethylene glycol dimethacrylate and 1.0 parts allyl thiourea were mixed at room temperature to provide a homogeneous solution. Then 0.016 parts of cumene hydroperoxide was added with spatulation to a 0.8 gram portion of the homogeneous solution and the sample cured as in Example 1. Color stability testing following the procedure of the preceding examples resulted in no observable color change after 39 hours exposure to ultraviolet light.

EXAMPLE 14

The following ingredients were added in the indicated order to a Silamat mechanical shaker manufactured by the Justi Company and then mixed for about one minute to prepare a homogeneous paste:

0.55 g. fused silica washed with 6N hydrochloric acid;

0.2 g. of a 71:29 parts by weight mixture of BIS-GMA and polyethyleneglycol dimethacrylate containing 4% by weight γ-methacryloxy propyltrimethoxysilane; and 0.002 g. allyl thiourea After the paste was removed from the shaker, 1 drop of cumene hydroperoxide solution in 1,6-hexanediol dimethacrylate (equivalent to 0.004 g. of cumene hydroperoxide) was added with spatulation to provide a composite. A 1/16 inch diameter hole was drilled in a bovine tooth. The hole was filled with the composite, covered with polyethylene terephthalate film, clamped and allowed to cure for 30 minutes. Then the tooth was broken with a hammer. All parts of the composite were hard and dry, indicating that a cure had been effected.

COMPARATIVE EXAMPLE

The general procedure of the preceding examples was followed in preparing a composition employing a redox system used in commercial dental composites. A homogeneous solution was prepared from 71 parts of BIS-GMA, 29 parts of polyethylene glycol dimethacrylate and 5 parts of γ-methacryloxypropyl trimethoxysilane. A paste was made by mixing 2.0 g. of the homogeneous solution with 5.5 g. of the fused silica described in Example 1. The paste was cured in the usual mold with 1% by weight benzoyl peroxide and 0.5% by weight 2,2'-(p-tolyimino)-diethanol, the per cent by weight being based on the sum of BIS-GMA and polyethylene glycol dimethacrylate. Testing for color stability following the procedure described in Example 1 revealed that the sample darkened considerably after 6 hours exposure to ultraviolet light.

What is claimed is:

1. A polymerizable dental composition having improved color stability consisting essentially of 20–100 parts by weight of at least one methacrylate monomer having 2 to 4 polymerizable double bonds, 0–80 parts by weight of inorganic particulate filler, 0–5.0% by weight based on said methacrylate monomer of silane coupling agent, 0.5–5.0% by weight based on said methacrylate monomer of hydroperoxide oxidizing agent and 0.3–2.0% by weight based on said methacrylate monomer of a substituted thiourea reducing agent having the formula

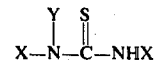

wherein X is hydrogen or Y and Y is $C_1$ to $C_8$ alkyl; $C_5$ or $C_6$ cycloalkyl; -chloro, -hydroxy- or mercapto- substituted $C_1$ to $C_8$ allyl; $C_3$ to $C_4$ alkenyl, $C_6$ to $C_8$ aryl; chloro-, hydroxy-, methoxy-, or sulfonyl substituted phenyl; $C_2$ to $C_8$ acyl; chloro-, or methoxy- substituted $C_2$ to $C_8$ acyl; $C_7$ to $C_8$ aralkyl; or chloro- or methoxy- substituted $C_7$ to $C_8$ aralkyl.

2. The composition of claim 1 having utility as a dental composite consisting essentially of
   20–25 parts by weight of at least one methacrylate monomer,
   75–80 parts by weight of said filler,
   3.0–5.0% by weight based on said methacrylate monomer of said silane coupling agent, 2.0–3.0% by weight based on said methacrylate monomer of said hydroperoxide oxidizing agent and 0.5–1.0% by weight based on said methacrylate monomer of said substituted thiourea reducing agent.

3. The composition of claim 1 wherein the methacrylate has a Brookfield viscosity at room temperature and 20 rpm of from about 100 to about 20,000 cps.

4. The composition of claim 3 wherein said oxidizing agent is characterized by having the peroxy group attached to a tertiary carbon atom.

5. The composition of claim 4 wherein said oxidizing agent is t-butyl hydroperoxide.

6. The composition of claim 4 wherein said oxidizing agent is cumene hydroperoxide.

7. The composition of claim 4 wherein said oxidizing agent is p-methane hydroperoxide.

8. The composition of claim 4 wherein said oxidizing agent is diisopropyl-benzene hydroperoxide.

9. The composition of claim 3 wherein said reducing agent is a monosubstituted thiourea.

10. The composition of claim 9 wherein said reducing agent is allyl thiourea.

11. The composition of claim 9 wherein said reducing agent is acetyl thiourea.

12. The composition of claim 9 wherein said reducing agent is phenyl thiourea.

13. The composition of claim 3 wherein said methacrylate monomer has two polymerizable double bonds.

14. The composition of claim 13 wherein said methacrylate is a mixture of the reaction product of bisphenol A and glycidyl methacrylate with tetraethylene glycol dimethacrylate, the oxidizing agent is cumenehydroperoxide and the reducing agent is acetyl thiourea.

15. The composition of claim 13 wherein said methacrylate is a mixture of the reaction product of bisphenol A and glycidyl methacrylate with 1,6-hexanediol dimethacrylate, the oxidizing agent is cumenehydroperoxide and the reducing agent is acetyl thiourea.

16. The cured composition of claim 1.

* * * * *